US00PP15946P2

(12) United States Plant Patent
Crist

(10) Patent No.: US PP15,946 P2
(45) Date of Patent: Sep. 6, 2005

(54) APPLE TREE NAMED 'WALDEN'

(50) Latin Name: *Malus domestica*
Varietal Denomination: Walden

(75) Inventor: Jeffrey D. Crist, Walden, NY (US)

(73) Assignee: Adams County Nursery, Inc., Aspers, PA (US)

( * ) Notice: Subject to any disclaimer, the term of this patent is extended or adjusted under 35 U.S.C. 154(b) by 27 days.

(21) Appl. No.: 10/818,802

(22) Filed: Apr. 6, 2004

(51) Int. Cl.[7] ..... A01H 5/00
(52) U.S. Cl. ..... Plt./161

(58) Field of Search ..... Plt./161

*Primary Examiner*—Anne Marie Grunberg
*Assistant Examiner*—Annette H Para
(74) *Attorney, Agent, or Firm*—James A. Lucas; Driggs, Lucas, Brubaker & Hogg Co., LPA

(57) ABSTRACT

A new and distinct strain of apple, designated 'Walden', originated as a whole tree mutation in a 'Honeycrisp' planting. The fruit are more attractively colored and glossier than parent tree fruit, which will greatly improve fresh fruit packout. Fruit color is solid scarlet red over 90 to 98 percent of the fruit surface compared to patchy red over a yellow-green background from parent trees. Color development is seven days earlier than 'Honeycrisp'.

2 Drawing Sheets

Latin name of genus and species: *Malus domestica.*
Variety name: 'Walden'.

BACKGROUND OF THE DISCLOSURE

This invention relates to apple trees and, more specifically, to an apple tree referred to as a strain, or bud mutation, of *Malus domestica* Borkh. 'Honeycrisp' (U.S. Plant Pat. No. 7,197).

I discovered this new and unique strain of apple tree as a whole tree mutation in a cultivated area near Milton, N.Y. The tree of this invention produces a fruit of attractive commercial value, with significantly earlier and brighter red color than the parent (U.S. Plant Pat. No. 7,197). Fruit red color development is seven days earlier than 'Honeycrisp'; however parent and new strain maturity development are similar. At harvest, percent red color is 90 to 98 percent compared to 60 to 70 percent on 'Honeycrisp', and skin finish is smoother.

This new strain of apple tree was asexually reproduced by grafting near Aspers, Pa., and such reproduction has shown this new strain to come true in two successive generations. This propagation of the new strain by grafting under standard controlled conditions clearly discloses the continued maintenance of the characteristics described herein which distinguish this new strain from the parent cultivar.

SUMMARY OF THE INVENTION

This new and distinctive strain of apple tree produces a fruit with brighter and more complete red color than 'Honeycrisp'. Fruit quality is exceptional, and harvest window is similar to that of the parent.

DESCRIPTION OF THE DRAWINGS

This new strain of apple tree is illustrated by the accompanying digital reproductions of photographic drawings, depicting the plant by the best possible color representation using color photography.

BOTANICAL DESCRIPTION OF THE PLANT

Figure 1:
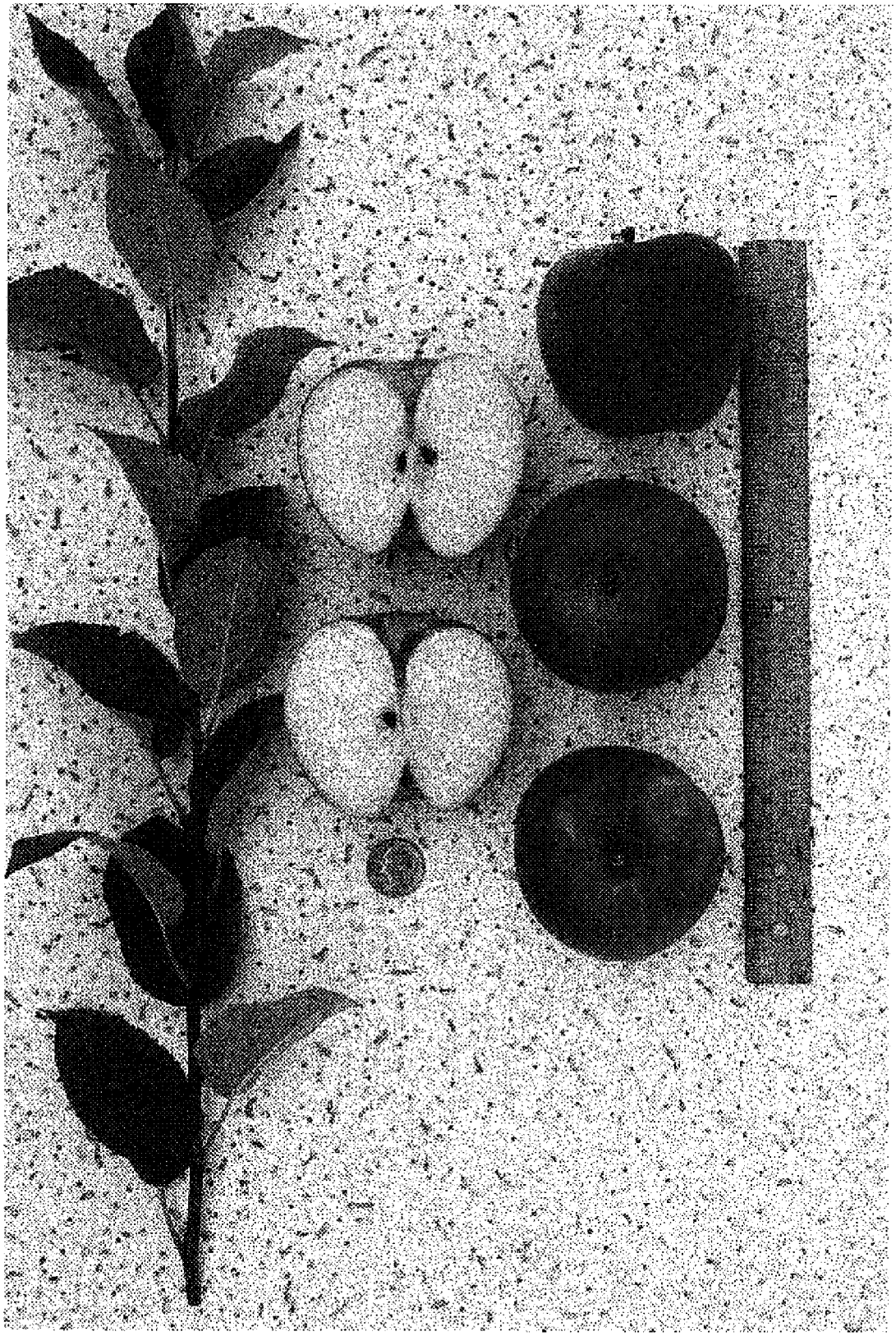
FIG. 1: At top, a terminal shoot showing current season's growth, leaves, leaf arrangement and leaf spacing; at center, a partially dissected fruit showing flesh and seed cavity; and at bottom, three whole fruit specimens in different orientations showing stem cavity, calyx and general shape and color.
Figure 2:
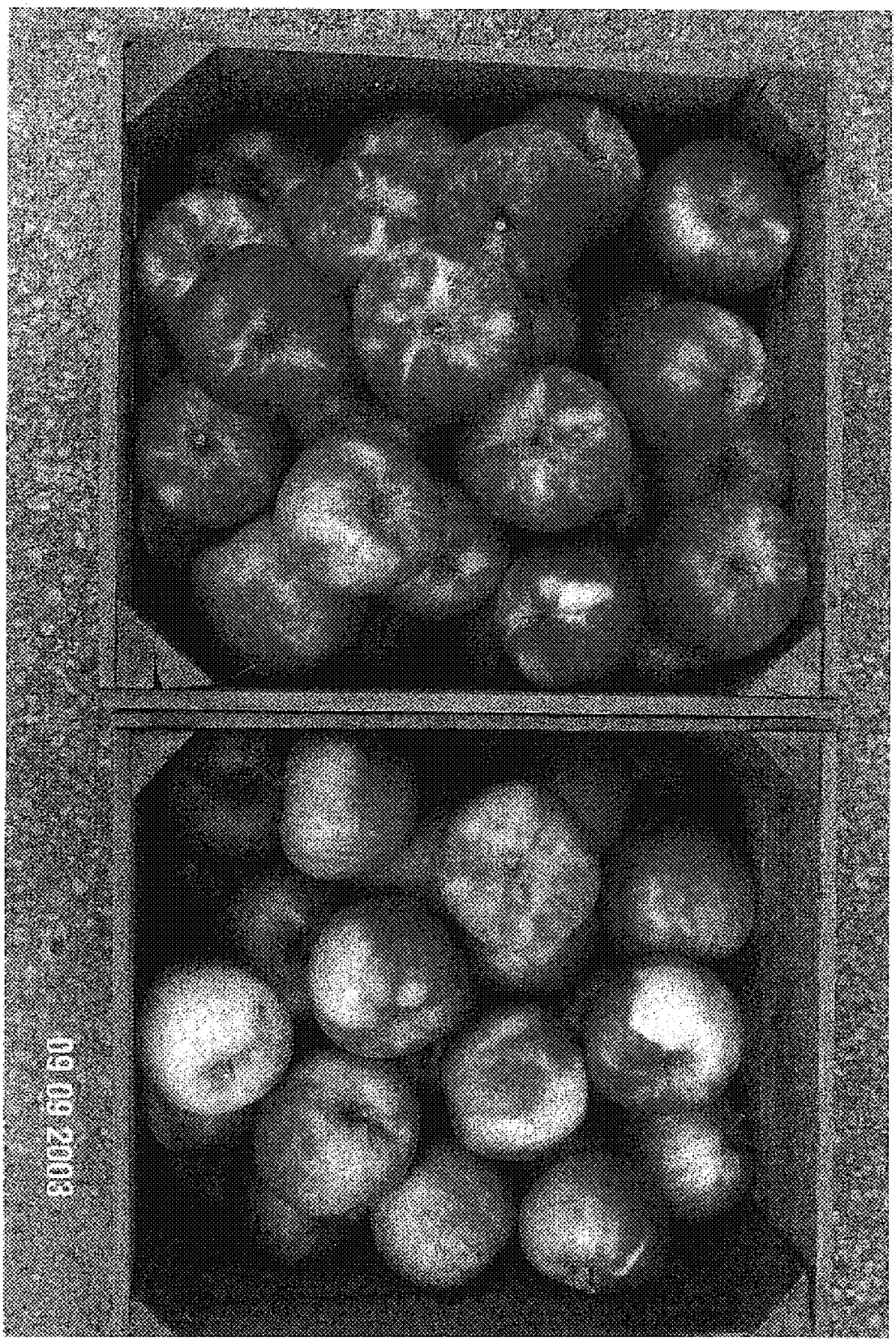
FIG. 2: On left, crate of new strain, compared to, on right, crate of 'Honeycrisp', harvested on the same date, representing characteristic background and blush color development.

All color references below are measured against The Royal Horticultural Society Colour Chart. Colors are approximate as color depends on horticultural practices such as light level and fertilization rate, among others.

Parentage: Whole tree mutation in a planting of 'Honeycrisp' trees. Asexually reproduced by bud grafting.

Tree: 2.7 m tall by 2.3 m wide and 6.8 kg fruit per tree, on seedling rootstock, at 4 years age, near Aspers, Pa. The rootstock is a domestic seedling (not patented). Upright-spreading tree of medium vigor, hardy, productive, annual bearer.

- *Trunk.*—Diameter 4.6 cm at 20 cm height above soil level, moderately smooth, gray, RHS (Royal Horticultural Society) 201A.

Branches:

- *Thickness.*—18 mm, average branching, 55–60 degree crotch angles, gray-orange, RHS 165A.
- *Lenticels.*—Approximately 22 per $cm^2$, slightly raised, 0.1 cm long.
- *Terminal shoots.*—Average length 45 cm, gray-orange, 165A.

Leaves:

- *Length.*—9 cm.
- *Width.*—6.5 cm. Semi-glossy, mostly flat, non-undulating, ovate with acuminate apex and rounded base, medium thick, dark green, RHS 137B for upper foliage surface, RHS 138B for lower surface, some having chlorotic margins and blotching.

*Venation.*—Reticulate pattern, green, RHS 138B.

*Margins.*—Serrate.

*Petioles.*—Length 2.5 cm, diameter 2 mm at mid-section, green, RHS 138B, some red at base.

*Stipules.*—0 to 2, length 8 mm, green, RHS 137B.

Reproductive organs:

*Anthers*—Length — 1-mm, Color— cream, RHS158B.

*Filaments.*—Length — 4 mm, Color— cream, RHS 158A.

*Pollen.*—Color— cream, RHS 158B.

*Pistil.*—Color— tan, RHS 164C.

*Styles.*—5, bunched, Length— 5 mm.

*Stigmas.*—Length— 1 mm.

*Ovary.*—Inferior.

Flowers:

*Dates of first and full blossoms.*—April 30 and May 3 in Aspers, Pa. in 2003. Midseason bloom period.

*Color.*—White, RHS 155D.

*Corolla diameter.*—3.0 cm.

*Pedicel length.*—2.5 cm.

*Flower petals.*—Shape ovate, width— 8 mm, length — 20 mm, texture soft.

*Fragrance.*—Mildly fragrant.

*Pollination.*—Cross pollination required; Pollinated by cultivars with similar bloom period.

*Buds.*—Ovoid, a few overlapping scales, length 4 mm, gray color, RHS 201D.

Fruit:

*Maturity when described.*—Ripe.

*Date.*—Sep. 8, 2003, same as 'Honeycrisp' (see accompanying figures comparing maturity indices).

*Uniformity of maturity.*—Requires only one harvest; must pick at proper maturity to avoid storage problems.

*Size.*—Uniformly large.

*Diameter.*—8 to 8.5 cm.

*Form.*—Mostly oblate, some conic, regular cross-section.

*Cavity.*—Flaring, depth 18 mm, breadth 15 by 20 mm, gold-russet markings.

*Stem.*—Gold, RHS 22A, some brown, RHS 177A, lightly pubescent, length 23 mm, diameter 2.5 mm, 0 bracts.

*Basin.*—Depth 14 mm, breadth 18 mm.

*Calyx.*—Mostly closed, sepals persistent with reflexed tips, diameter 5 mm.

*Sepals.*—Aristulate, length— 5 mm; Color— green RHS 138B.

*Skin.*—Medium thick, more glossy than 'Honeycrisp', medium cuticle wax.

*Lenticels.*—Small to medium size, moderate number, circular, white, RHS 155B, scattered over most of surface, more numerous near basin.

*Russet.*—Slight, mainly around cavity, gold, RHS 163B.

*Ground color.*—Yellow-green, RHS 1C.

*Color markings.*—Solid blush (compared to patchy red color on 'Honeycrisp') over 90 to 98% of surface, bright scarlet red, RHS 57A, some blotches.

*Bloom.*—Scant.

*Scarfskin.*—Occasional.

*General color effect.*—Brilliant scarlet red over most of fruit surface with gold stem cavity.

*Flesh.*—Juicy, cream color, RHS 159D.

*Texture.*—Firm, medium grained, crisp.

*Flavor.*—Delicious tart/sweet blend.

*Aroma.*—Mildly aromatic.

*Eating quality.*—Exceptional, 13 to 14% soluble solids, 16 to 17 lbs firmness at harvest maturity.

*Core.*—Equidistant between calyx and stem ends.

*Carpellary area.*—Visible.

*Depth of calyx tube.*—10 mm.

*Seed cells.*—Axile, closed, 5 in number.

*Cell walls.*—Thin, obovate to lanceolate in longitudinal section, narrow in cross-section (length 9 mm, breadth 3 mm), surface non-tufted.

Seeds: Usually 10, length 6 mm, breadth 2.5 mm, form acute.

*Color.*—Brown, RHS 166A.

Uses: Excellent for fresh wholesale and retail markets.

Keeping quality: Similar to 'Honeycrisp' in nearby planting.

Resistance to insects: Similar to 'Honeycrisp'.

Resistance to diseases: Similar to 'Honeycisp'.

Other observations: Very winter hardy, moderate tolerance to drought and heat, moderate susceptibility to storage disorders (similar to parent).

I claim:

1. A new and distinct strain of apple tree, as illustrated and described, characterized by improved fruit color and skin finish.

* * * * *